(12) United States Patent
Taubmann et al.

(10) Patent No.: US 12,213,827 B2
(45) Date of Patent: Feb. 4, 2025

(54) METHOD AND DATA PROCESSING SYSTEM FOR PROVIDING A STROKE INFORMATION

(71) Applicant: Siemens Healthcare GmbH, Erlangen (DE)

(72) Inventors: Oliver Taubmann, Weilersbach (DE); Hendrik Ditt, Neustadt an der Aisch (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 325 days.

(21) Appl. No.: 17/764,326

(22) PCT Filed: Sep. 18, 2020

(86) PCT No.: PCT/EP2020/076154
§ 371 (c)(1),
(2) Date: Mar. 28, 2022

(87) PCT Pub. No.: WO2021/063709
PCT Pub. Date: Apr. 8, 2021

(65) Prior Publication Data
US 2022/0395244 A1    Dec. 15, 2022

(30) Foreign Application Priority Data
Sep. 30, 2019  (EP) .................................... 19200370

(51) Int. Cl.
*A61B 6/00* (2024.01)
*A61B 6/50* (2024.01)
(Continued)

(52) U.S. Cl.
CPC ............ *A61B 6/5211* (2013.01); *A61B 6/501* (2013.01); *G06T 7/0016* (2013.01); *G06T 7/30* (2017.01);
(Continued)

(58) Field of Classification Search
USPC .......................................................... 382/131
See application file for complete search history.

(56) References Cited

U.S. PATENT DOCUMENTS

| 2012/0114205 A1 | 5/2012 | Tang et al. |
| 2018/0025255 A1 | 1/2018 | Poole et al. |

(Continued)

FOREIGN PATENT DOCUMENTS

| CN | 109191422 A | 1/2019 |
| KR | 20190068254 A | 6/2019 |

OTHER PUBLICATIONS

Kuang Hulin et al: "Segmenting Hemorrhagic and Ischemic Infarct Simultaneously From Follow-Up Non-Contrast CT Images in Patients With Acute Ischemic Strake"; IEEE Access; vol. 7;pp. 39842-39851; Aug. 4, 2019; XP011717831.

(Continued)

*Primary Examiner* — Jacky X Zheng
(74) *Attorney, Agent, or Firm* — Harness, Dickey & Pierce, P.L.C.

(57) ABSTRACT

At least one example embodiment relates to a computer-implemented method for providing stroke information, the method comprising
 receiving computed tomography imaging data of an examination area of a patient, the examination area of the patient comprising a plurality of brain regions, at least one brain region of the plurality of brain regions being affected by a stroke,
 receiving brain atlas data,
 generating registered imaging data based on the computed tomography imaging data and the brain atlas data, the registered imaging data being registered to the brain atlas data,
 generating the stroke information regarding the stroke based on a set of algorithms and the registered imaging data, and
 providing the stroke information.

19 Claims, 3 Drawing Sheets

(51) Int. Cl.
  *G06T 7/00* (2017.01)
  *G06T 7/30* (2017.01)
(52) U.S. Cl.
  CPC ............... *G06T 2207/10081* (2013.01); *G06T 2207/20081* (2013.01); *G06T 2207/20084* (2013.01); *G06T 2207/30016* (2013.01); *G06T 2207/30101* (2013.01)

(56) References Cited

U.S. PATENT DOCUMENTS

| | | |
|---|---|---|
| 2018/0253530 A1 | 9/2018 | Goldberg et al. |
| 2019/0099145 A1* | 4/2019 | Kim ........................ A61B 6/504 |
| 2019/0122363 A1* | 4/2019 | Greveson ............... A61B 6/032 |

OTHER PUBLICATIONS

Aspectsinstroke.com, Aspect Score for Assessment in acute stroke, http://www.aspectsinstroke.com/.
Rapid Aspects; https://www.rapidai.com/rapid-aspects; Automatic Identification of ASPECTS Regions and Scores.
brainomix.com, e-aspects, software tool to support scoring, https://brainomix.com/e-aspects.
Zhang Zhenwei et al: "Radiological images and machine learning: Trends, perspectives, and prospects"; Computers in Biology and Medicine; vol. 108; Mar. 27, 2019; pp. 354-370; XP085691877; ISSN: 0010-4825; DOI: 10.1016/J.COMPBIOMED.2019.02.017.
Wu Jufang "Diagnosis valuble of CT perfusion imaging combined with CTA for acute ischemic stroke"; 1673-9701 (2016) 12-0108-04;.

* cited by examiner

METHOD AND DATA PROCESSING SYSTEM FOR PROVIDING A STROKE INFORMATION

CROSS-REFERENCE TO RELATED APPLICATIONS

This application is the National Phase under 35 U.S.C. § 371 of PCT International Application No. PCT/EP2020/076154, which has an international filing date of Sep. 18, 2020, which designated the United States of America, and which claims priority to European patent application EP 19200370.5 filed Sep. 30, 2019, the entire contents of each of which are hereby incorporated herein by reference.

FIELD

At least one example embodiment relates to computer-implemented methods for providing stroke information, data processing systems, computer program products and computer-readable mediums.

BACKGROUND

Stroke remains one of the leading causes of death in developed countries. Nearly nine out of ten strokes are ischemic, i.e. they are caused by a thrombus (blood clot) occluding a vessel, thereby preventing part of the brain from being supplied with oxygenated blood.

Typically, stroke patients first undergo a non-contrast computed tomography (CT) head scan for initial assessment. In case of an ischemic stroke, it is essential to quickly identify which parts of the brain are affected in order to choose the most promising treatment. However, this is a fairly challenging task as the early signs of ischemia in non-contrast scans are often subtle. A CT angiography (CTA) scan is usually performed to reliably determine the affected regions, assess the collateral status and localize the thrombus. An additional CT perfusion (CTP) can be useful, for example, for predicting the core, i.e. necrotic tissue, and penumbra (hypoxic, but potentially salvageable tissue) of an ischemic stroke, but is not widely adopted in clinical practice.

Assessment of ischemic stroke in non-contrast scans is typically performed by visual inspection, often guided by the ASPECT score (Alberta Stroke Program Early CT score). The ASPECT score is an established clinical tool that defines 10 regions of both brain hemispheres to check for early stroke signs in order to compute a quantitative score between 0 and 10 quantifying the severity of the stroke. It is specific to the brain area supplied by the anterior circulation.

Determining whether a region is affected is, to a considerable degree, subjective. Several software tools exist to support this scoring with standardized computations of gray level differences between both hemispheres. Some also offer a segmentation of the affected area within the pre-defined ASPECT regions. Finding the thrombus in non-contrast or CTA scans is typically still a manual task that can take valuable time.

SUMMARY

An underlying technical problem is to facilitate an assessment of stroke that is improved with regard to automation and reliability. This problem is solved by the subject matter of the independent claims. The dependent claims are related to further example embodiments.

At least one example embodiment relates to a computer-implemented method for providing stroke information, the method comprising Receiving computed tomography imaging data of an examination area of a patient, the examination area of the patient comprising a plurality of brain regions, at least one brain region of the plurality of brain regions being affected by a stroke, Receiving brain atlas data, Generating registered imaging data based on the computed tomography imaging data and the brain atlas data, the registered imaging data being registered to the brain atlas data, Generating the stroke information regarding the stroke based on a set of algorithms and the registered imaging data, and Providing the stroke information.

At least one example embodiment relates to a computer-implemented method for providing stroke information is hereby disclosed, the method comprising Receiving computed tomography imaging data of an examination area of a patient, the examination area of the patient comprising a plurality of brain regions, at least one brain region of the plurality of brain regions being affected by a stroke, Generating the stroke information regarding the stroke based on a set of algorithms and the computed tomography imaging data, and Providing the stroke information.

In particular, the generating of the stroke information regarding the stroke can be further based on the brain atlas data. The brain atlas data can be, for example, probabilistic brain atlas data. The generating of the registered imaging data, can comprise, for example, a segmenting of the plurality of brain regions based on the computed tomography imaging data, thereby generating, for each brain region of the plurality of brain regions, a representation of that brain region. The generating of the registered imaging data, can comprise, for example, a scaling the computed tomography imaging data and/or a rigid pre-registration of the computed tomography imaging data.

The generating of the registered imaging data, can comprise, for example, a rigid or non-rigid registration of the computed tomography imaging data to the brain atlas data. Thereby a common coordinate system can be provided to which the computed tomography data, the brain atlas data and/or training data, on which a trained machine learning model is based, can be related.

The computed tomography imaging data can comprise, for example, at least one non-contrast computed tomography image and/or computed tomography angiography (CTA) data, in particular digital subtraction computed tomography angiography data. The CTA data can be related to a single phase or to multiple phases. The computed tomography imaging data can further comprise, for example, computed tomography perfusion data and/or spectral computed tomography imaging data. Spectral computed tomography imaging data can be based, for example, on dual-energy, in particular, dual-source, computed tomography imaging and/or photon-counting computed tomography imaging.

The brain atlas data can comprise, for example, at least one of a vessel probability map, vessel labels and an average local density map. The set of algorithms can comprise one or more algorithms.

The stroke information can comprise, for example, at least one of a location of the blood clot, a name of a vessel comprising the blood clot, a marking of a region affected by the blood clot, a value and/or a graphical representation related to a density reduction of brain tissue.

In another example embodiment, the method for providing stroke information further comprises receiving, in addition to the computed tomography imaging data, medical information related to the patient. The medical information can comprise, for example, an onset time of a stroke that has occurred in the brain, and/or a result of a prior medical assessment, in particular a non-imaging-based prior medical assessment, of the examination area (e.g. NIHSS—National Institutes of Health Stroke Scale) and/or a set of physiological parameters of the patient.

In another example embodiment the method further comprises
- Generating mirrored imaging data based on a left-right mirroring of the computed tomography imaging data and/or the registered imaging data,
- Calculating a left-right difference image based on the computed tomography imaging data and the mirrored imaging data,
- wherein the stroke information is generated further based on the left-right difference image.

The calculating of the left-right difference image can comprise, for example, a rigid or non-rigid registration of the mirrored imaging data to the computed tomography imaging data and/or a smoothing of the mirrored imaging data and/or the computed tomography imaging data.

Based on the left-right difference image, an asymmetry between both hemispheres can be visualized.

In case the computed tomography imaging data comprises CTA data, based on the left-right difference image, a location of a blood clot of a vessel can be determined as the vessels downstream of the occlusion will be missing only on the cerebral hemisphere that is affected by the stroke, and/or an extent of the infarcted brain region can be determined as the affected tissue will be darker than the corresponding region on the contralateral side.

In case the computed tomography imaging data comprises at least one non-contrast computed tomography image, the extent of the infarcted brain region can be determined (similar to the CTA case above), in particular if some time has passed since the onset of the stroke, for example, roughly 2.5 hours, and/or a density reduction with respect to the contralateral side can be determined.

In another example embodiment the method further comprises
- Calculating, for each brain region of the plurality of brain regions, a local density average of that brain region based on the computed tomography imaging data and/or the registered imaging data,
- Calculating, for each brain region of the plurality of brain regions, a density difference information of that brain region based on the local density average of that brain region and the local density average of at least one other brain region of the plurality of brain regions, thereby obtaining a density difference map,
- wherein the stroke information is generated further based on the density difference map.

In another example embodiment the method further comprises
- Calculating, for each brain region of the plurality of brain regions, a local density average of that brain region based on the computed tomography imaging data and/or the registered imaging data,
- Calculating, for a reference brain region, a density average of the reference brain region based on the computed tomography imaging data and/or the registered imaging data, the examination area of the patient comprising the reference brain region,
- Calculating, for each brain region of the plurality of brain regions, a density difference information of that brain region based on the local density average of that brain region and the density average of the reference brain region, thereby obtaining a density difference map,
- wherein the stroke information is generated further based on the density difference map.

In another example embodiment the method further comprises
- Receiving a reference density difference map, wherein the stroke information is generated further based on the density difference map and the reference density difference map.

According to another example embodiment, the reference brain region comprises, for each brain region of the plurality of brain regions, a respective subregion, such that a plane that is perpendicular to a sagittal plane of the patient is located between that brain region and the respective subregion.

The sagittal plane of the patient can be, for example, a midsagittal plane of the patient, the midsagittal plane of the patient being located between the left cerebral hemisphere and the right cerebral hemisphere.

The plane that is perpendicular to the sagittal plane of the patient can be, for example a coronal plane of the patient or a transverse plane of the patient or a linear combination of a coronal plane of the patient and a transverse plane of the patient.

According to a another example embodiment, the reference brain region comprises, for each brain region of the plurality of brain regions, a respective subregion, such that that brain region and the respective subregion are located within the same cerebral hemisphere.

The reference brain region can comprise at least one further brain region, the plurality of brain regions not comprising the at least one further brain region. The reference brain region can comprise, for example, one or more or all brain regions of the plurality of brain regions. The reference brain region can extend, for example, over an entire cross-section of the brain of the patient.

If the reference brain region is one brain region of the plurality of brain regions, the action of calculating, for each brain region of the plurality of brain regions, a local density average of that brain region based on the computed tomography imaging data and/or the registered imaging data can comprise the action of calculating, for a reference brain region, a density average of the reference brain region based on the computed tomography imaging data and/or the registered imaging data, the examination area of the patient comprising the reference brain region.

The coronal plane can be, for example, a mid-coronal plane.

According to one example, each brain region of the plurality of brain regions is located anterior with respect to the coronal plane and the reference brain region or the subregion of the reference brain region is located posterior with respect to the coronal plane.

According to another example, each brain region of the plurality of brain regions is located posterior with respect to the coronal plane and the reference brain region or the subregion of the reference brain region is located anterior with respect to the coronal plane.

The density difference information of any brain region of the plurality of brain regions can comprise, for example, an absolute and/or relative difference of the local density average of that brain region and the density average of the reference brain region.

The density difference information of any brain region of the plurality of brain regions can comprise, for example, an absolute and/or relative difference of the local density average of that brain region and the local density average of the at least one other brain region of the plurality of brain regions.

The density difference information of any brain region of the plurality of brain regions can comprise, for example, an absolute and/or relative difference of the local density average of that brain region and a global density average.

The global density average can be calculated, for example, based on the respective local density average of each brain region of the plurality of brain regions.

The global density average can be, for example, the density average of the reference brain region.

For example, relative differences regarding the local density average can be calculated based on CTA data. For example, absolute and/or relative differences regarding the local density average can be calculated based on the at least one non-contrast computed tomography image.

The density difference information of each brain region of the plurality of brain regions can be calculated, for example, further based on the brain atlas data and/or a statistical comparison of that brain region with the at least one other brain region of the plurality of brain regions. In particular, for each brain region of the plurality of brain regions an atlas-based local density average of that brain region can be calculated based on the brain atlas data and/or a comparison result of that brain region can be calculated based on a comparing of the local density average of that brain region and the atlas-based local density average of that brain region. In this case, the density difference information of any brain region of the plurality of brain regions can comprise, for example, the comparison result of that brain region.

The density difference map can comprise, for each brain region of the plurality of brain regions, the respective density difference information. Based on the density difference map, stroke information can be obtained that is robust to an individual variation of density. Based on the density difference map, abnormalities can be revealed that may not be detected by left-right asymmetry analysis, e.g. in case of prior infarcts or occlusions that affect both hemispheres.

In another example embodiment the set of algorithms comprises an algorithm for calculating an onset time of the stroke,
wherein the onset time of the stroke is calculated by applying the algorithm for calculating an onset time of a stroke onto the left-right difference image and/or onto the density difference map,
wherein the stroke information comprises the calculated onset time of the stroke and/or is generated further based on the calculated onset time of the stroke.

In particular, the onset time of the stroke can be calculated in case it is unavailable as an input in form of the medical information related to the patient. For example, a density reduction can be calculated based on the left-right difference image and/or based on the density difference map. Then the water uptake quantification can be calculated based on the density reduction. Based on the water uptake quantification, the onset time of the stroke can be calculated.

In another example embodiment the set of algorithms comprises an algorithm for generating a representation of a blood clot,
wherein the representation of the blood clot is generated by applying the algorithm for generating the representation of the blood clot onto the registered imaging data and the brain atlas data,
wherein the stroke information comprises the representation of the blood clot and/or is generated further based on the representation of the blood clot.

The algorithm for generating the representation of the blood clot can be based, for example, on an image-to-image model that maps input non-contrast CT imaging/CTA data to the representation of the blood clot and can be trained, for example, based on annotated ground truth imaging data in which one or more blood clots are segmented. The algorithm for generating the representation of the blood clot can be configured, for example, to use the at least one non-contrast computed tomography image as mandatory input and the CTA data as optional input. This may be realized as a single model trained on both inputs, but designed to handle missing input, or as two separate sub-models whose output is merged when both the mandatory input and the optional input are available.

The representation of the clot can be, for example, a mask image of the clot. Based on the representation of the blood clot, the location and/or the size of the blood clot, in particular in form of a thrombus, can be determined. A label of the occluded vessel can be determined by automatically looking up the vessel label in the brain atlas data at the found location of the blood clot.

In another example embodiment the set of algorithms comprises an algorithm for generating a clot composition information,
wherein the clot composition information is generated by applying the algorithm for generating the clot composition information onto the registered imaging data and the representation of the blood clot,
wherein the stroke information comprises the clot composition information and/or is generated further based on the clot composition information.

In particular, the clot composition information can be based on and/or comprise a degree of calcification of the blood clot. The algorithm for generating the clot composition can be configured to analyze at least one of a shape, a density and a texture of the blood clot to generate the clot composition information that characterizes the clot composition.

In case the computed tomography imaging data comprises spectral computed tomography imaging data, the clot composition information can be generated based on spectral information, for example, based on a decomposition of materials of the representation of the blood clot.

In another example embodiment the set of algorithms comprises an algorithm for generating a viability map, the viability map being indicative, for each brain region of the plurality of brain regions, of a brain tissue viability of that brain region,
wherein the viability map is generated by applying the algorithm for generating the viability map onto the registered imaging data and the brain atlas data,
wherein the stroke information comprises the viability map and/or is generated further based on the viability map.

Based on the viability map, the at least one brain region that is affected by the stroke can be determined. The viability map may comprise, for each brain region of the plurality of brain regions of the brain, a probability regarding the brain tissue viability of that brain region, in particular a probability that the brain tissue of that brain region belongs to either core or penumbra.

The algorithm for generating the viability map can be based, for example, on an image-to-image model that maps input non-contrast CT imaging/CTA data to the viability map. From the viability map, location and size of the at least one brain region that is affected by the stroke can be determined.

The algorithm for generating the viability map can be trained, for example, based on a plurality of training datasets, each dataset of the plurality of training datasets comprising at least one training non-contrast CT image and/or training CTA data as a training input and a training viability map generated, for example, based on CT perfusion data and/or follow-up CT imaging data, as a training output. The CTA data as an optional training input can be handled as described above for the algorithm for generating the representation of the blood clot.

If multiple CTA phases are available, the confidence of the brain tissue viability estimation can be improved. While regions with neither early nor late enhancement are likely non-viable, regions with late enhancement only (due to slower distribution of the contrast medium via collaterals) may still be salvageable.

If structured, non-imaging-based prior assessment of the patient is received, this can be utilized to reduce the likelihood of false positives (both in terms of affected regions and blood clots). For instance, the brain hemisphere that is affected by the stroke may be known in advance. Prior assessment may yield probabilities regarding which brain regions may be affected by the stroke. This can be cross-checked with the viability map.

In another example embodiment the method further comprises
  Generating an output-output consistency information based on an output of an algorithm of the set of algorithms and an output selected from the group consisting of the left-right difference image, the density difference map and an output of at least one other algorithm of the set of algorithms,
  wherein the stroke information is generated based on the output-output consistency information.

In particular, the output-output consistency information can be generated based on a cross-check of the output of the algorithm of the set of algorithms and the output selected from the group consisting of the left-right difference image, the density difference map and the output of the at least one other algorithm of the set of algorithms. The output-output consistency information can be further generated based on the registered image and/or the brain atlas data.

In particular, the algorithm of the set of algorithms can be an algorithm for processing the at least one non-contrast computed tomography image and/or the at least one other algorithm of the set of algorithms can be an algorithm for processing the computed tomography angiography data.

For example, the output of the algorithm of the set of algorithms can be generated by applying the algorithm of the set of algorithms onto the at least on non-contrast computed tomography image and/or the output of the at least one other algorithm of the set of algorithms can be generated by applying the at least one other algorithm of the set of algorithms onto the computed tomography angiography data.

In one example, the output-output consistency information can be generated based on an output of the algorithm for generating the representation of the blood clot, the left-right difference image and the brain atlas data. In particular, a blood clot location that has been determined based on the left-right difference image and the brain atlas data can be used to increase a fidelity of the algorithm for generating the representation of the blood clot, for example, in form of a prior probability for the blood clot location or in form of an elimination of false positive outputs of the algorithm for generating the representation of the blood clot.

In another example, the output-output consistency information can be generated based on an output of the algorithm for generating the viability map and the left-right difference image and/or based on an output of the algorithm for generating the viability map and the density difference map. In particular, the consistency information can be indicative of a consistency of the viability map with respect to the left-right difference image and/or the density difference map.

In another example, the output-output consistency information can be generated based on an output of the algorithm for generating the representation of the blood clot and an output of the algorithm for generating the viability map. In particular, the consistency information can be indicative of a consistency of the representation of the blood clot and the viability map, for example be indicative of whether the affected regions according to the viability map are plausible in view of the blood clot location according to the representation of the blood clot (Would vessels downstream of the presumed occlusion supply blood to these regions?)—and vice versa.

Identifying implausible combinations allows finding likely false positives. The brain atlas data can comprise blood flow information indicative of which regions might be supplied by which vessels. The blood flow information can be probabilistic to account for anatomical variation.

In another example embodiment the method further comprises
  Receiving prior information regarding the stroke,
  Generating an input-output consistency information based on the prior information and an output selected from the group consisting of the left-right difference image, the density difference map and an output of an algorithm of the set of algorithms,
  wherein the stroke information is generated based on the input-output consistency information.

In particular, the input-output consistency information can be generated based on a cross-check of the prior information and the output selected from the group consisting of the left-right difference image, the density difference map and the output of the algorithm of the set of algorithms.

The prior information can comprise, for example, an onset time of the stroke. The onset time of the stroke can be used to calculate an expected degree of density reduction. The algorithm of the set of algorithms can be, for example, an image-processing algorithm.

If an onset time is received as prior information, it can be used to calculate an expected degree of density reduction which can be compared to the corresponding reduction observed in the left-right difference image and/or the density difference map.

Based on the output-output consistency information and/or the input-output consistency information the reliability of the stroke information can be further improved.

In another example embodiment the method further comprises
  Generating, for at least one algorithm of the set of algorithms, an attention map, the attention map being indicative, for each image region of a plurality of image regions of the registered imaging data, of a contribution of that image region to an output of the at least one algorithm, Providing the attention map of each algorithm of the set of algorithms.

In order to make the results transparent and traceable, an attention map, for example in form of a saliency map, can be computed to visualize which image regions in which image contributed the most to arriving at the output of a given algorithm. The attention map can be visualized, for example, as an overlay on the at least one non-contrast computed tomography image and/or the CTA data. The attention map can be used to visually explain which parts of the registered imaging data were most influential for the output of the at least one algorithm, thereby facilitating reasoning and explicable results.

The at least one algorithm can be selected, for example, from the group consisting of the algorithm for calculating an onset time of a stroke, the algorithm for generating a representation of a blood clot, the algorithm for generating a clot composition information and the algorithm for generating a viability map.

The attention map can be generated, for example, based on a machine learning model, in particular a neural network model, on which the at least one algorithm is based. The attention map can be generated, for example, further based on an input, onto which the at least one algorithm is applied, and/or an output of the at least one algorithm, the output corresponding to the input. In a simple case, the attention map can be generated based on a derivative of the output of the at least one algorithm with respect to voxels of the corresponding input.

In another example embodiment at least one algorithm of the set of algorithms is based on a trained machine learning model, wherein the generating of the stroke information regarding the stroke is based on the trained machine learning model and the registered imaging data. In particular, the generating of the stroke information regarding the stroke based on the trained machine learning model and the registered imaging data can comprise applying the trained machine learning model onto the registered imaging data.

In another example embodiment the generating of the stroke information regarding the stroke is further based on the brain atlas data. In particular, the generating of the stroke information regarding the stroke based on the trained machine learning model, the registered imaging data and the brain atlas data can comprise applying the trained machine learning model onto the registered imaging data and the brain atlas data.

In particular, any of the algorithm for calculating an onset time of a stroke, the algorithm for generating a representation of a blood clot, the algorithm for generating a clot composition information and the algorithm for generating a viability map can be based on a respective machine learning model.

Concerning the machine learning model, various architectures and/or other ways of structuring the input and output similar to the ones described are conceivable. The machine learning model can be based on a deep neural network and/or another technique, for example random forest regression. For localization of blood clots, a classifier/detector approach may be used as well, potentially followed by a distinct segmentation step that may or may not be machine-learning based itself. The machine learning model can be based, for example, on an image-to-image model, for example, with an encoding path followed by a decoding path, where individual stages are coupled by skip connections.

Any of the algorithms mentioned herein can be based on one or more of the following architectures: convolutional neural network, deep belief network, random forest, deep residual learning, deep reinforcement learning, recurrent neural network, Siamese network, generative adversarial network or auto-encoder. In particular, the trained machine learning model can be embodied as a deep learning model, in particular as a deep convolutional neural network.

In another example embodiment the trained machine learning model is based on a plurality of training datasets, each training dataset of the plurality of training datasets comprising a training input in form of training computed tomography imaging data and a corresponding training output in form of a training stroke information. In particular, the trained machine learning model can be trained based on a plurality of training datasets, each training dataset of the plurality of training datasets comprising a training input in form of training computed tomography imaging data and a corresponding training output in form of a training stroke information.

In another example embodiment, a computer-implemented method for providing a trained machine learning model is hereby disclosed, comprising Receiving a plurality of training datasets, each training dataset of the plurality of training datasets comprising a training input in form of training computed tomography imaging data and a corresponding training output in form of a training stroke information, Training the machine learning model based on the plurality of training datasets, and Providing the trained machine learning model.

The training computed tomography imaging data can comprise, for example, at least one training non-contrast computed tomography image and/or training CTA data.

The training stroke information can be determined, for example based on computed tomography perfusion data and/or based on related follow-up scans. The training stroke information can comprise, for example, an annotation, in particular an annotation of a blood clot and/or a vessel and/or a brain region. Such annotations can be provided by expert readers. In another example embodiment one of the left and right cerebral hemispheres is selected, wherein onto each of those training datasets of the plurality of training datasets, for which the cerebral hemisphere, that is affected by a respective stroke, does not correspond to the selected cerebral hemisphere, a left-right mirroring is applied, in particular to make the hemisphere, that is affected by the respective stroke, corresponding to the selected cerebral hemisphere.

The left-right mirroring can be applied onto any training dataset, for example, by applying the left-right mirroring onto the training input of that training dataset and onto the training output of that training dataset. With regard to a part of the training dataset, that is represented in form of a number and/or a text, the left-right mirroring can be understood as a left-right interchanging, if applicable. Each left-right mirrored training dataset can be used for training the machine learning model instead of the respective original training dataset.

This allows exploiting of symmetry properties of the brain and reducing the complexity that the machine learning model is required to learn.

For example, the images of the training datasets can be first brought in the coordinate system of the brain atlas data by non-rigid reformation to reduce irrelevant variation due to positioning and anatomy. Registered images are then left-right mirrored (flipped), if necessary, such that the affected hemisphere always appears on the same, pre-defined side, for example left. In this way, the machine learning model does not have to learn the same features twice for comparing a stroke sign on the left cerebral hemisphere with its healthy counterpart on the right cerebral hemisphere, and vice versa.

In another example embodiment for each of the training datasets of the plurality of training datasets—a normalization information is calculated based on the respective training input and the brain atlas data and
 a normalization is applied onto the respective training input based on the normalization information, thereby obtaining a normalized training input,
 wherein a normalization information for the registered imaging data is calculated based on the registered imaging data and the brain atlas data,
 wherein the generating of the stroke information regarding the stroke is further based on the normalization information for the registered imaging data.

Each normalized training input can be used for training the machine learning model, in particular instead of the respective original training input. In particular, the generating of the stroke information regarding the stroke based on the trained machine learning model, the registered imaging data and the normalization information for the registered imaging data can comprise applying the trained machine learning model onto normalized registered imaging data, the normalized registered imaging data being obtained by applying the normalization onto the registered imaging data based on the normalization information for the registered imaging data.

By determining an estimate of the average gray value of the patient's healthy brain tissue and comparing it to the corresponding density in the brain atlas data, a normalization scale and offset can be found that allows standardizing the input intensities to the level of the brain atlas data. As this needs to be done prior to the training of the machine learning model, the distinction between healthy and affected tissue can be derived from a preliminary assessment based on left-right comparison, in particular for one-sided infarcts, and/or a comparison of local vs. global density.

At least one example embodiment relates to a data processing system for providing stroke information, the data processing system comprising
 an imaging data receiver for receiving computed tomography imaging data of an examination area of a patient, the examination area of the patient comprising a plurality of brain regions, at least one brain region of the plurality of brain regions being affected by a stroke,
 a brain atlas receiver for receiving brain atlas data,
 a registered-image generator for generating registered imaging data based on the computed tomography imaging data and the brain atlas data, the registered imaging data being registered to the brain atlas data,
 a stroke-information generator for generating the stroke information regarding the stroke based on a set of algorithms and the registered imaging data,
 a stroke-information provider for providing the stroke information.

In another example embodiment, a data processing system for providing stroke information is hereby disclosed, the data processing system comprising
 an imaging data receiver for receiving computed tomography imaging data of an examination area of a patient, the examination area of the patient comprising a plurality of brain regions, at least one brain region of the plurality of brain regions being affected by a stroke,
 a stroke-information generator for generating the stroke information regarding the stroke based on a set of algorithms and the computed tomography imaging data,
 a stroke-information provider for providing the stroke information.

In another example embodiment the data processing system is configured to implement the method according to one or more of the disclosed example embodiments.

At least one example embodiment relates to a medical imaging device comprising a data processing system for providing stroke information according to one or more of the disclosed aspects. The medical imaging device may be, for example, a computed tomography device or a combination of different medical imaging modalities, for example, a PET-CT-imaging device.

At least one relates to a computer program product comprising program elements which induce a data processing system to carry out the steps of the method according to one or more of the disclosed example embodiments, when the program elements are loaded into a memory of the data processing system.

At least one example embodiment relates to a computer-readable medium on which program elements are stored that can be read and executed by a data processing system, in order to perform the steps of the method according to one or more of the disclosed example embodiments, when the program elements are executed by the data processing system.

Any of the components of the data processing system mentioned herein or any interface between the components of the data processing system can be embodied in form of hardware and/or software. In particular, an interface can be embodied in form of at least one of a PCI-Bus, a USB or a Firewire. In particular, a unit can comprise hardware elements and/or software elements, for example a microprocessor, a field programmable gate array (an acronym is "FPGA") or an application specific integrated circuit (an acronym is "ASIC").

The data processing system can, for example, comprise at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Calculations for performing a step of a method and/or for training a machine learning model may be carried out in a processor.

Data, in particular, the computed tomography data, the brain atlas data, the prior information regarding the stroke and the plurality of training datasets, can be received, for example, by receiving a signal that carries the data and/or by reading the data from a computer-readable medium. Data, in particular, the stroke information and the attention map, can be provided, for example, by transmitting a signal that carries the data and/or by writing the data into a computer-readable medium and/or by displaying the data on a display.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable medium can be embodied as non-permanent main memory (e.g. random-access memory) or as permanent mass storage (e.g. hard disk, USB stick, SD card, solid state disk).

The proposed solution allows a standardized, fully automated and comprehensive assessment of ischemic stroke cases based on native CT scans. Both non-contrast computed tomography imaging data and CTA data can be considered in a joint fashion and/or cross-checked with regard to each other. The proposed solution is applicable, in particular, to occlusions in the anterior and in the posterior regions of the brain and is not limited to a specific brain region, the specific brain region being defined, for example, by the artery supplying that specific brain region.

Wherever not already described explicitly, individual embodiments, or their individual aspects and features, can be combined or exchanged with one another without limiting or widening the scope of example embodiments, whenever such a combination or exchange is meaningful and in the sense of these example embodiments. Advantages which are described with respect to one embodiment are, wherever applicable, also advantageous of other embodiments.

In the context of example embodiments, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

Reference is made to the fact that the described methods and the described units are merely preferred example embodiments and that example embodiments can be varied by a person skilled in the art, without departing from the scope of example embodiments specified by the claims.

BRIEF DESCRIPTION OF THE DRAWINGS

At least some example embodiments will be illustrated below with reference to the accompanying figures using example embodiments. The illustration in the figures is schematic and highly simplified and not necessarily to scale.

DETAILED DESCRIPTION

Figure 1:
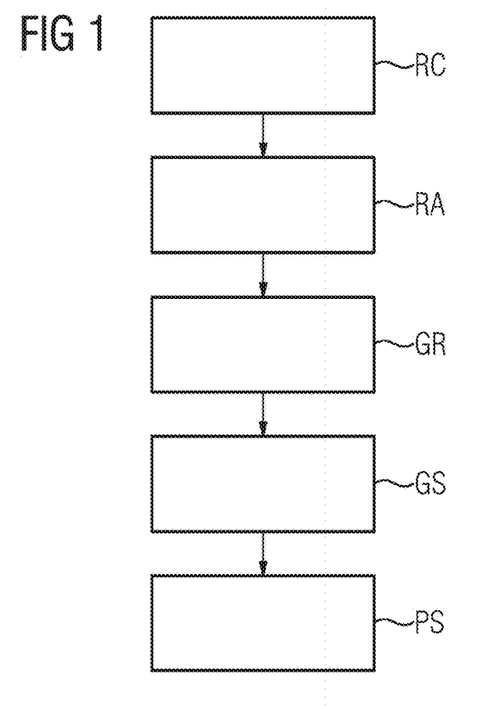
FIG. 1 shows a diagram illustrating a computer-implemented method for providing stroke information.

FIG. 1 shows a diagram illustrating a computer-implemented method for providing stroke information, the method comprising Receiving RC computed tomography imaging data of an examination area of a patient, the examination area of the patient comprising a plurality of brain regions, at least one brain region of the plurality of brain regions being affected by a stroke, Receiving RA brain atlas data, Generating GR registered imaging data based on the computed tomography imaging data and the brain atlas data, the registered imaging data being registered to the brain atlas data, Generating GS the stroke information regarding the stroke based on a set of algorithms and the registered imaging data, Providing PS the stroke information.

Figure 2:
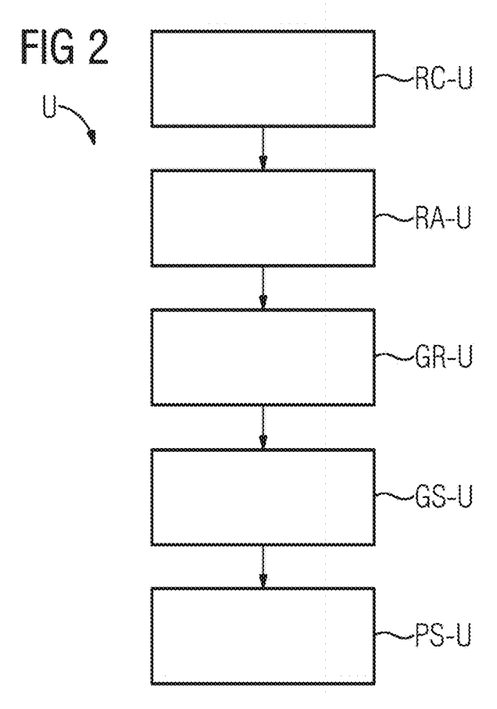
FIG. 2 shows a data processing system for providing a prediction of a medical target variable.

FIG. 2 shows a data processing system U for providing a prediction of a medical target variable, the data processing system comprising an imaging data receiver RC-U for receiving RC computed tomography imaging data of an examination area of a patient, the examination area of the patient comprising a plurality of brain regions, at least one brain region of the plurality of brain regions being affected by a stroke, a brain atlas receiver RA-U for receiving RA brain atlas data, a registered-image generator GR-U for generating GR registered imaging data based on the computed tomography imaging data and the brain atlas data, the registered imaging data being registered to the brain atlas data, a stroke-information generator GS-U for generating GS the stroke information regarding the stroke based on a set of algorithms and the registered imaging data, a stroke-information provider PS-U for providing PS the stroke information.

Figure 3:
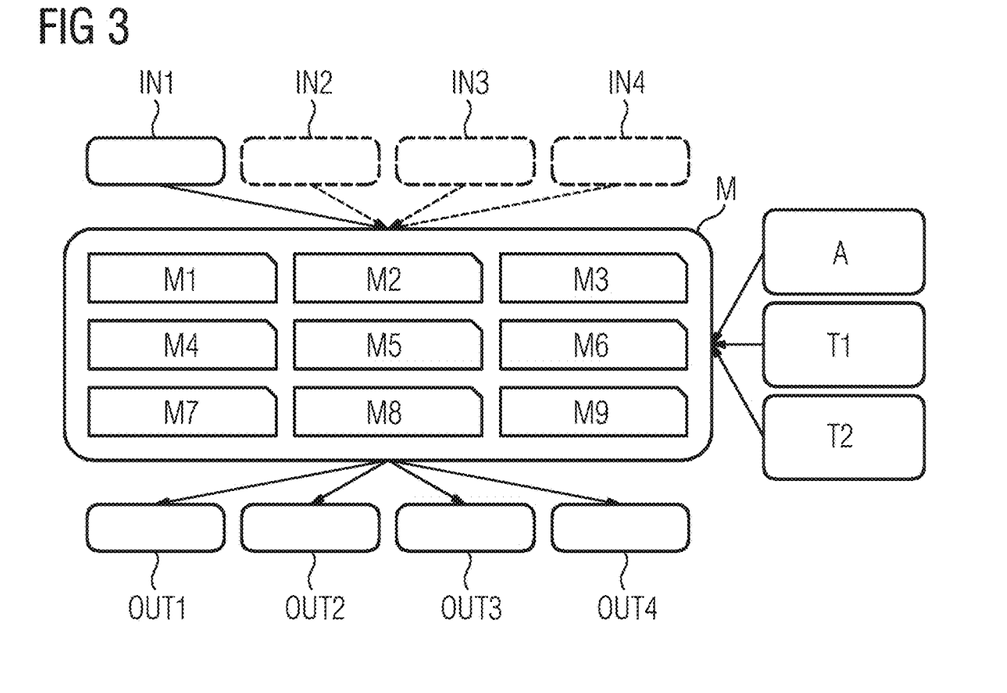
FIG. 3 shows an overview of inputs, outputs, resources and algorithmic components of the method for providing stroke information.

FIG. 3 shows an overview of exemplary inputs, outputs, resources and algorithmic components of the method for providing stroke information.

Exemplary inputs are the non-contrast computed tomography image IN1, in particular in form of volume image, the CTA data IN2, in particular in form of CTA volume data, the stroke onset time IN3 and the information from prior assessment IN4, in particular in form of NIHSS data. For those inputs that are represented with dashed lines, the method is configured to handle missing inputs.

Exemplary algorithmic components are the atlas registration M1, the left-right comparison M2, the local vs. global density comparison M3, the infarct segmentation model M4, the clot segmentation model M5, the clot composition characterization M6, the saliency map computation M7, the onset time calculation M8 and the establishing of consistency M9. These exemplary algorithmic components form the set of algorithms M.

Exemplary resources are the brain atlas A comprising a probabilistic vessel map and vessel labels, the training data T1 based on perfusion and/or follow-up scans, and the training data T2 based on blood clot annotations.

Exemplary outputs are the first output OU1, comprising the clot location, size and composition, the second output OUT2, comprising the name of the occluded vessel, the third output OUT3, comprising a marking of the affected regions, a predicted tissue viability and an estimated onset time, and the fourth marking OUT4, comprising a visualization, for example in form of an attention map, of individual inputs' contributions to the output of the corresponding algorithm. These exemplary outputs form the stroke information for the case shown.

Figure 4:
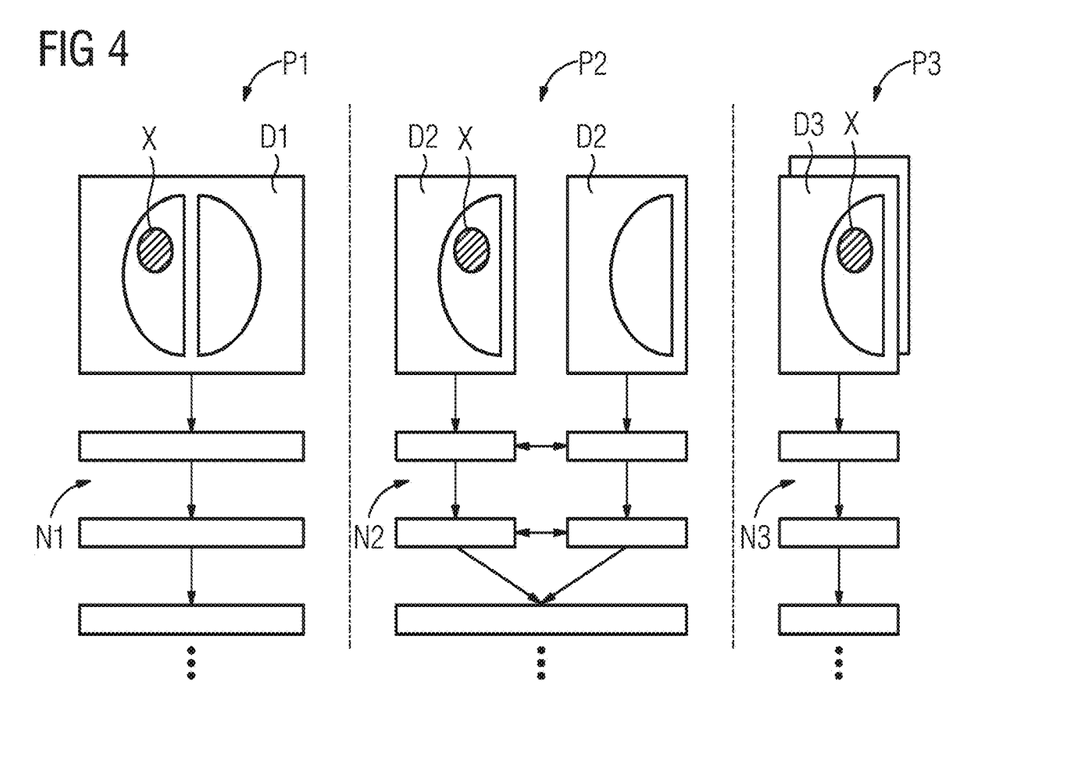
FIG. 4 shows an overview of different configurations of training inputs for training the machine learning model.

FIG. 4 shows an overview of different configurations of training inputs for training the machine learning model.

According to the configuration P1, the training input D1 is fed into the network N1 as one image comprising both the left cerebral hemisphere and the right cerebral hemisphere. One of the two cerebral hemispheres comprises brain tissue X that is affected by the stroke. The other one of the two cerebral hemispheres is unaffected by the stroke.

According to configuration P2, the training input D2 is split into a sub-image for the left cerebral hemisphere and a sub-image for the right hemisphere, that first go through distinct legs of the network (though possibly with the same network weights shared in both legs) before being merged to a single path, e.g. by concatenation or subtraction. This facilitates comparisons between both cerebral hemispheres as the network is structured such that it first analyzes each side individually before comparing the extracted features of both. The training input D2 can be pre-processed such that one of the two legs receives the sub-images of the hemisphere comprising the affected brain tissue X and the other one of the two legs receives the sub-images hemisphere that is unaffected by the stroke, independently from which of the left and right hemisphere comprises the affected brain tissue X and in matching orientations.

According to the configuration P3, the sub-images of the training input D3 are stacked on top of each other as two channels before being fed into the network N3, with corresponding areas being aligned on both channels. This is another way to facilitate left-right comparisons as local operations such as convolutions will operate on corresponding regions on both hemispheres.

Any of the configurations P1, P2 and P3 can be used with both slice-wise 2D models as well as fully volumetric 3D models.

The output of the network may also be modeled in any of the described variants. It can then be reformatted in such a way as to first bring it back into the space of the atlas, from which it can be propagated back into the coordinate space of the original scan so that it can be shown as an overlay or an individual image aligned with the input.

Figure 5:
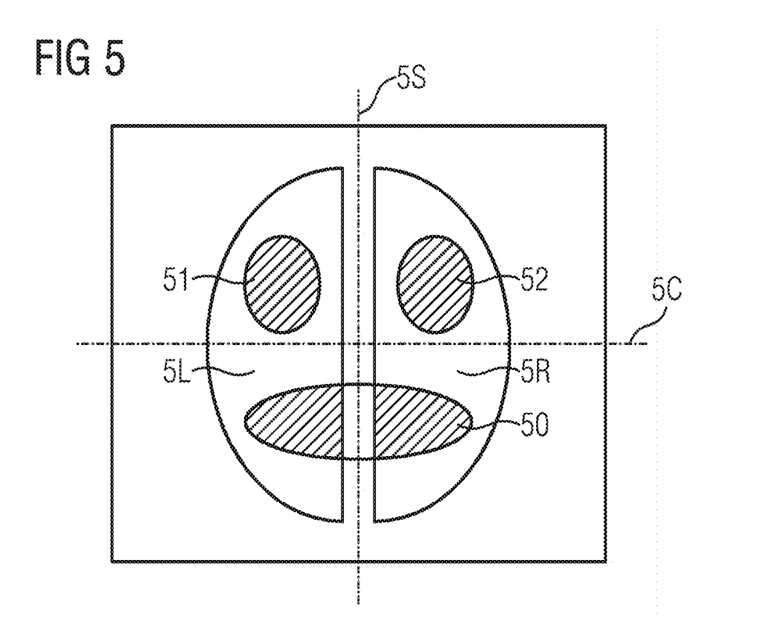
FIG. 5 shows a plurality of brain regions and a reference brain region.

FIG. 5 shows a plurality of brain regions 51, 52 and a reference brain region 50.

The plane 5C that is perpendicular to the sagittal plane 5S of the patient is located between the brain region 51 and a first subregion of the reference brain region 50, in particular between the brain region 51 and the reference brain region 50.

The plane 5C that is perpendicular to the sagittal plane 5S of the patient is located between the brain region 52 and a second subregion of the reference brain region 50, in particular between the brain region 52 and the reference brain region 50.

The sagittal plane 5S of the patient is a midsagittal plane of the patient, the midsagittal plane of the patient being located between the left cerebral hemisphere 5L and the right cerebral hemisphere 5R. The plane 5C is a coronal plane of the patient.

The brain region 51 and the first subregion of the reference brain region 50 are located within the left cerebral hemisphere 5L. The brain region 52 and the second subregion of the reference brain region 50 are located within the right cerebral hemisphere 5R.

The invention claimed is:

1. A computer-implemented method for providing stroke information, the method comprising:
   receiving computed tomography imaging data of an examination area of a patient, the examination area of the patient comprising a plurality of brain regions, at least one brain region of the plurality of brain regions being affected by a stroke;
   receiving brain atlas data;
   generating registered imaging data based on the computed tomography imaging data and the brain atlas data, the registered imaging data being registered to the brain atlas data;
   generating the stroke information regarding the stroke based on a set of algorithms and the registered imaging data; and
   providing the stroke information.

2. The method according to claim 1, further comprising:
   calculating, for each brain region of the plurality of brain regions, a local density average of the brain region based on at least one of the computed tomography imaging data or the registered imaging data;
   calculating, for a reference brain region, a density average of the reference brain region based on at least one of the computed tomography imaging data or the registered imaging data, the examination area of the patient comprising the reference brain region; and
   calculating, for each brain region of the plurality of brain regions, a density difference information of the brain region based on the local density average of the brain region and the density average of the reference brain region, thereby obtaining a density difference map,
   wherein the stroke information is generated further based on the density difference map.

3. The method according to claim 2,
   wherein the reference brain region comprises, for each brain region of the plurality of brain regions, a respective subregion, such that a plane that is perpendicular to a sagittal plane of the patient is located between that brain region and the respective subregion.

4. The method according to claim 2,
   wherein the reference brain region comprises, for each brain region of the plurality of brain regions, a respective subregion, such that the brain region and the respective subregion are located within the same cerebral hemisphere.

5. The method according to claim 1, further comprising:
   generating mirrored imaging data based on a left-right mirroring of at least one of the computed tomography imaging data or the registered imaging data; and
   calculating a left-right difference image based on the computed tomography imaging data and the mirrored imaging data,
   wherein the stroke information is generated further based on the left-right difference image.

6. The method according to claim 5,
   wherein the set of algorithms comprises an algorithm for calculating an onset time of the stroke,
   the onset time of the stroke is calculated by applying the algorithm for calculating the onset time of the stroke onto at least one of the left-right difference image or the density difference map, and
   the stroke information at least one of comprises the calculated onset time of the stroke or is generated further based on the calculated onset time of the stroke.

7. The method according to claim 1,
   wherein the set of algorithms comprises an algorithm for generating a representation of a blood clot,
   the representation of the blood clot is generated by applying the algorithm for generating the representation of the blood clot onto the registered imaging data and the brain atlas data, and
   the stroke information at least one of comprises the representation of the blood clot or (ii) is generated further based on the representation of the blood clot.

8. The method according to claim 7,
wherein the set of algorithms comprises an algorithm for generating clot composition information,
the clot composition information is generated by applying the algorithm for generating the clot composition information onto the registered imaging data and the representation of the blood clot, and
the stroke information at least one of comprises the clot composition information or (ii) is generated further based on the clot composition information.

9. The method according to claim 1, further comprising:
generating an output-output consistency information based on an output of an algorithm of the set of algorithms and an output selected from a group consisting of a left-right difference image, a density difference map and an output of at least one other algorithm of the set of algorithms,
wherein the stroke information is generated based on the output-output consistency information.

10. The method according to claim 1, further comprising:
receiving prior information regarding the stroke; and
generating an input-output consistency information based on the prior information and an output selected from a group consisting of a left-right difference image, a density difference map and an output of an algorithm of the set of algorithms,
wherein the stroke information is generated based on the input-output consistency information.

11. The method according to claim 1,
wherein at least one algorithm of the set of algorithms is based on a trained machine learning model, and
the generating of the stroke information regarding the stroke is based on the trained machine learning model and the registered imaging data.

12. The method according to claim 11,
wherein the trained machine learning model is based on a plurality of training datasets, each training dataset of the plurality of training datasets comprising a training input in form of training computed tomography imaging data and a corresponding training output in form of a training stroke information.

13. The method according to claim 12,
wherein one of left and right cerebral hemispheres is selected, and
onto each of those training datasets of the plurality of training datasets, for which the cerebral hemisphere that is affected by a respective stroke does not correspond to the selected cerebral hemisphere, a left-right mirroring is applied.

14. The method according to claim 12,
wherein for each of the training datasets of the plurality of training datasets:
a normalization information is calculated based on the respective training input and the brain atlas data and
a normalization is applied onto the respective training input based on the normalization information, thereby obtaining a respective normalized training input, and
a normalization information for the registered imaging data is calculated based on the registered imaging data and the brain atlas data,
the generating of the stroke information regarding the stroke is further based on the normalization information for the registered imaging data.

15. A data processing system configured to implement the method of claim 1.

16. A non-transitory computer program product comprising program elements that, when executed by a data processing system, cause the data processing system to perform the method of claim 1.

17. A non-transitory computer-readable medium storing program elements that can be read and executed by a data processing system, in order to perform the method of claim 1, when the program elements are executed by the data processing system.

18. A data processing system configured to provide stroke information, the data processing system comprising:
an imaging data receiver configured to receive computed tomography imaging data of an examination area of a patient, the examination area of the patient comprising a plurality of brain regions, at least one brain region of the plurality of brain regions being affected by a stroke;
a brain atlas receiver configured to receive brain atlas data;
a registered-image generator configured to generate registered imaging data based on the computed tomography imaging data and the brain atlas data, the registered imaging data being registered to the brain atlas data;
a stroke-information generator configured to generate the stroke information regarding the stroke based on a set of algorithms and the registered imaging data; and
a stroke-information provider configured to provide the stroke information.

19. A data processing system configured to provide stroke information, the data processing system comprising:
a memory storing computer-readable instructions; and
at least one processor configured to execute the computer-readable instructions to cause the data processing system to,
receive computed tomography imaging data of an examination area of a patient, the examination area of the patient comprising a plurality of brain regions, at least one brain region of the plurality of brain regions being affected by a stroke,
receive brain atlas data,
generate registered imaging data based on the computed tomography imaging data and the brain atlas data, the registered imaging data being registered to the brain atlas data,
generate the stroke information regarding the stroke based on a set of algorithms and the registered imaging data, and
provide the stroke information.

* * * * *